United States Patent [19]

Fabinski et al.

[11] Patent Number: 5,163,601

[45] Date of Patent: Nov. 17, 1992

[54] MAKING A MEASURING CHAMBER

[75] Inventors: Walter Fabinski, Kriftel; Gunther Bernhardt, Frankfurt, both of Fed. Rep. of Germany

[73] Assignee: Hartmann & Braun, Frankfurt, Fed. Rep. of Germany

[21] Appl. No.: 712,927

[22] Filed: Jun. 7, 1991

[30] Foreign Application Priority Data

Jun. 11, 1990 [DE] Fed. Rep. of Germany ....... 4018610

[51] Int. Cl.$^5$ ............................................. B23K 31/02
[52] U.S. Cl. ................................... 228/124; 228/187; 228/246; 228/263.12
[58] Field of Search ............... 228/120, 122, 124, 187, 228/219, 246, 263.12, 563

[56] References Cited

U.S. PATENT DOCUMENTS

| | | | |
|---|---|---|---|
| 2,751,514 | 6/1956 | Atlee | 228/187 |
| 4,717,860 | 1/1988 | Christgau et al. | 228/124 |
| 4,722,632 | 2/1988 | Campbell | 228/122 |
| 4,757,292 | 7/1988 | Basil, Jr. et al. | 228/124 |
| 4,883,218 | 11/1989 | Dunn et al. | 228/124 |

Primary Examiner—Samuel M. Heinrich
Attorney, Agent, or Firm—R. H. Siegemund

[57] ABSTRACT

A method for making a gas chamber for photometric measuring equipment comprises providing a metal frame with recesses on opposite sides establishing a web and at least one opening in the web and having solder surface areas; providing at least two calcium fluoide panes, said panes each having a rim portion; is improved by providing rim surface portions of the panes about to face the recess-web portion of said metal frame with a plurality of layers, by (i) physical vapor depositing a thin chromium nickel layer, (ii) physical vapor depositing thereon a nickel layer, and (iii) by physical vapor depositing thereon a gold layer; vapor depositing on the web portion around the opening of said recesses a gold layer; providing at least two solder elements of basically ring-shaped configuration respectively to be interposed between the web and the panes, the soldering elements being configured so that between their respective outer contour and walls of the recesses a solder flow space obtains when the solder elements are placed into the recesses; and soldering the element on one side for solder-connecting the respective pane to the web at a temperature of about 213° C. in an inert gas and the other element on the other side of and to the web and the respective other pane at a soldering temperature at about 170° C. in an inert gas.

2 Claims, 1 Drawing Sheet

MAKING A MEASURING CHAMBER

BACKGROUND OF THE INVENTION

The present invention relates to the making of a sample or measuring chamber or cuvette to be used in photometric and/or spectrometric or spectrographic measuring equipment. Devices of the kind to which the invention pertains need sealed chambers which hold a gas in a well defined concentration in a tightly sealed manner so that the gas will not be diluted or diffused to the exterior of the chamber. Such a sample or measuring chamber is usually made of metal and has a particular length.

Since the purpose of the chamber is to subject a specific amount of gas to radiation for purposes of absorption of some of the radiation by the gas, it is necessary that the chamber have front and rear sides provided with windows. For example, calcium fluoride $CaF_2$ is provided for such a window, i.e. as the window pane. Of course, the windows must be gas-tightly sealed vis-a-vis the metal body of which the chamber is made. The measuring effect results, of course, from the absorption of light passing through this chamber and through the windows, the absorption being carried out by the enclosed gas. Since the gas concentration and quantity are to be constant, there is a correspondingly high degree of constancy of absorption.

A variety of technologies are known for the construction of such measuring chambers (see for example U.S. Pat. No. 5,003,175). The state of the art is given in a data sheet and user's manual by applicant's assignee. It lists as known a device traded under the designation 42/22-22-0.9.79 for use in a gas analyzer called "Radas 1G" by the Isami Corporation. And here, on page 40, a calibrating chamber is described as including quartz and transmission glasses. A gas is permanently enclosed, i.e. supposedly trapped and confined after the chamber has been closed through melting. However, such a melting procedure for purposes of closing the chamber is not suitable if the chamber contains hydrocarbons or Nox gases. These gases change when subjected to temperatures as high as required for melting quartz or glass. On the other hand, quartz and glass are not suitable for passing medium range infrared radiation instead of visible light. This is so because infrared radiation is already absorbed at wave lengths of about 4.5 micrometers, that is, in a band of about 2.5 micrometers. For that reason also, a sapphire is usable only to a very limited extent. Its absorption edge is situated at about 5.5 micrometers and will therefore be insufficiently capable of acquiring information of the absorption spectrum of $SO_2$ and many hydrocarbons.

German printed Patent Application 30 10 516 describes a measuring chamber for optical gas analyzers wherein the radiation-permeable windows are connected by means of a glass solder used as a brazing material providing the connection of the windows to an intermediate frame. The thus prepared windows are then gas-tightly connected to the measuring chamber proper through regular solder or brazing. On the other hand, German printed Patent Application 27 20 636 describes radiation-permeable windows of calcium or barium fluoride.

Owing to its transparency to infrared radiation, particularly in the median infrared range up to a wave length of about 8 micrometers, fluorite is occasionally used as end windows in a measuring chamber. This arrangement does indeed permit ascertaining the absorption sprectra of most gases of interest as far as measuring technology and data acquisition is concerned. Also, this particular material is suitable because it is not hygroscopic and has no catalytic properties vis-a-vis the usual filling contained in the chamber.

DESCRIPTION OF THE INVENTION

It is an object of the present invention to provide a new and improved method for making a non-catalytically effective gas-tight sample or measuring chamber under utilization of a joint or connection that can be soldered in a temperature range below 220 degrees Centigrade involving the connection between fluorite and a metal frame.

It is a specific object of the present invention to provide a new and improved method for making a sample and measuring chamber for photometric measuring devices having the following features: the chamber to be improved is provided with windows which are gas-tightly connected to a chamber frame itself, and made of calcium fluoride, which chamber is to include a gas of well of defined concentration to be maintained confined and trapped therein in unvarying concentration.

In accordance with the preferred embodiment of the present invention, the connection and gas-tight sealing is provided as follows. The windows or, more specifically, the window panes, are cleaned by means of ultrasonics under utilization of tensides, next they are metallized at the particular soldering surfaces where they will be connected to the container or frame under utilization of a physical vapor depositing or pvd method according to which the following layers are deposited. A chromium nickel layer is first provided at a thickness of about 50 nanometers. Thereon, a nickel layer is deposited at a thickness of about 200 nanometers, and on top of the latter, a gold layer is deposited at a thickness of about 30 nanometers. On the other hand, a soldering surface of the measuring chamber and frame is prepared by depositing an activation protective layer of gold of about 30 nanometers next to an excess solder capturing space. Solder components are provided with a certain excess as far as the amount needed for soldering is concerned, and soldering itself is carried out in the vapor phase of an inert liquid and at a temperature of about 230° C. for soldering one side of the container frame and a temperature of 170° C. is used for soldering the window pane to the second side of the container frame.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is drawn on a larger scale compared to the perspective view of FIG. 1.

Proceeding now to the detailed description of the drawings, FIG. 1 illustrates a measuring chamber for photometric measuring equipment. The particular container is basically constructed as a rectangular frame 1 made of metal such as brass or a suitable brass alloy. Frame 1 is basically flat and is provided on both flat sides 11 and 12 with two shallow recesses leaving thinned web portions such as 8. These recesses are of square-shaped configuration with rounded corners, and the web portions are in turn provided with circular or shallow cylindrical openings 2 each of which is subdivided through a thin diagonal bar such as 21.

Figure 1:
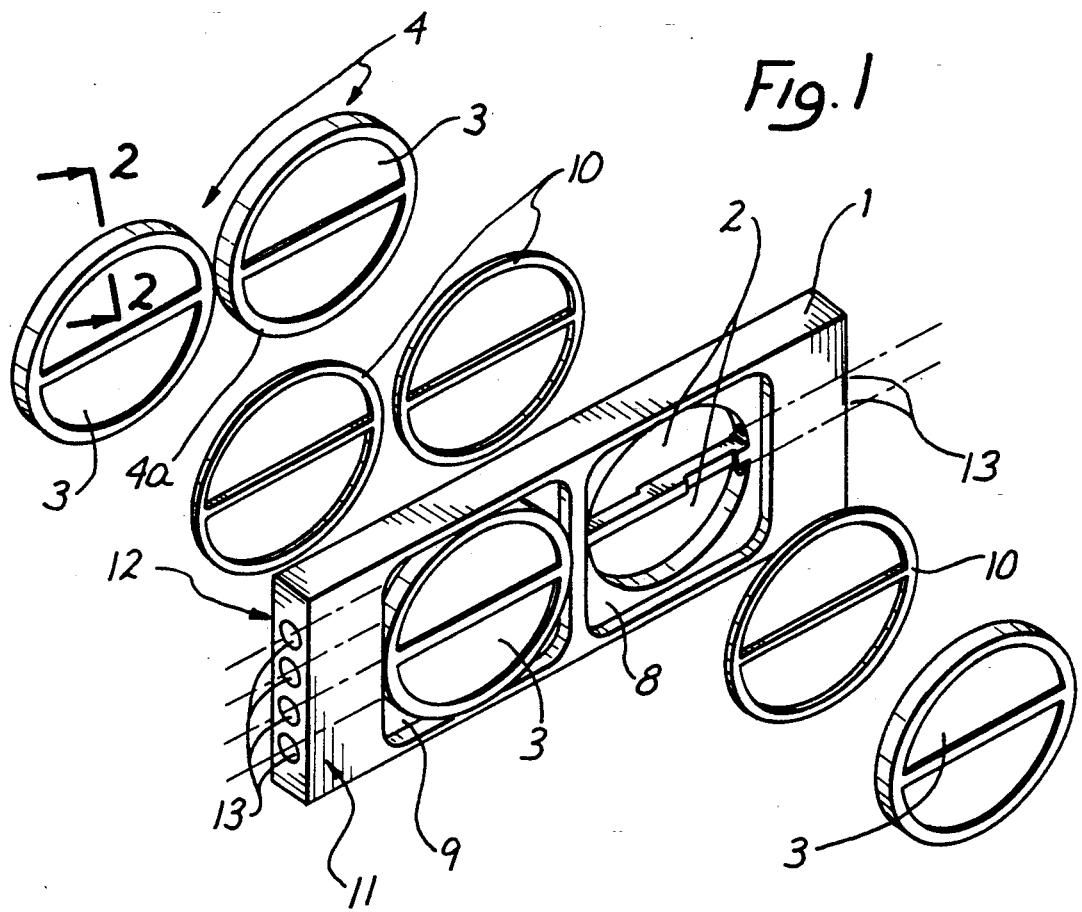
FIG. 1 illustrates an exploded view of a measuring chamber constructed in accordance with the preferred embodiment of the present invention in which the best mode of the invention is practiced.

The space or openings 2 are to become gas chambers; i.e. they are to become confined spaces for containing gas or gasses in well defined concentrations. The container frame 1, moreover, is constructed to accommodate windows, i.e. window panes in the recesses of the flat sides 11 and 12 so that radiation can penetrate this chamber in a direction transverse to the flat dimensions of this brass or brass alloy container frame 1. The chambers proper are semi-circular openings in the web-like thinner portions such as 8 of the container body 1.

These semi-circular openings 2 have to be closed on both sides, that is, 11 and 12, through panes 3 which are permeable to whatever radiation is used in the measuring equipment. It is assumed that these panes are made of calcium fluoride, $CaF_2$. Therefore the various chambers are defined, for example, each by a semi-circular arch 2a, a cross-bar surface 2b and window panes 3 on both sides. Within such an enclosure for an opening 2, gas is contained which is actually fed to the various chambers (there are altogether four) through bores 13.

Reference number 10 refers to elements which can be designated as solder components or solder-assist parts which constitute a connecting medium which, on being liquified, will ultimately connect the metal container frame 1 to the calcium fluoride panes 3; the gas-tight connection of these elements is the main purpose and object of the invention. Because function and long-term duration of sealing of the measuring chambers are decisive factors for the quality of this measuring chamber and since they depend on the quality and property of the connection and bond between the panes and the metal container, it is necessary to proceed very carefully and deliberately in the making of these solder connections.

The method to be described next, particularly involving preparation and carrying out of soldering, is believed to maximize at the present state of the art the long-term constancy of the properties of gas-filled measuring of this kind. The result has been tested and it is believed that the method steps establish indispensable prerequisites for obtaining an adequate product as far as function is concerned.

One begins by cleaning the panes 3. As stated, these panes are made of calcium fluoride and cleaning involves ultrasonic treatment within a tenside solution. The panes 3 in this arrangement (there are altogether four), are of a circular configuration and are provided with circular edges or annular rims 4 as well as crossbar portions. These rims or edges constitute part of the pane. Certain surface portions 4a will be metallized through a physical vapor deposit method and in the following fashion.

Figure 2:
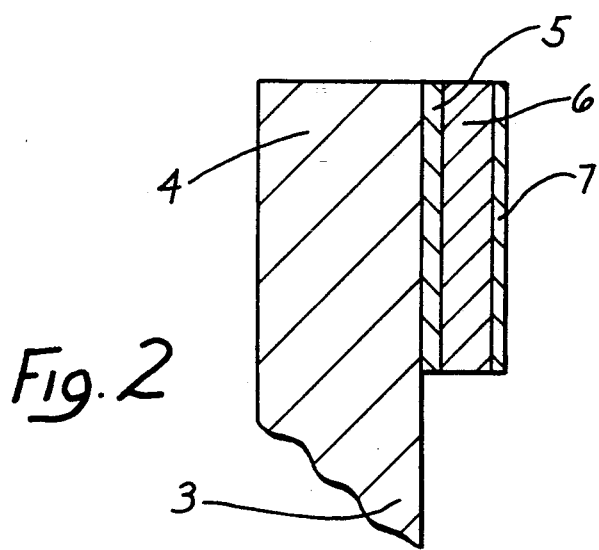
FIG. 2 illustrates a cross section through the end coatings as they are applied to the windows. Moreover.

At first, a chromium nickel layer 5 is deposited, about 50 nanometers thick, to establish an annular coating, with a cross bar, as can be seen also from FIG. 2. On top of this layer 5 is provided nickel layer 6 of about 200 nanometers and a thinner gold layer 7 is vapor-deposited on top of layer 6, the gold layer being of about 30 nanometers thick. The drawing for FIG. 2 shows these various layers in terms of thickness on a comparable relative scale.

The web surface 8 is now in addition provided with an activation protective layer of gold of a thickness of about 30 nanometers on both sides of the webs and directly covering the rim portion as well as the crossbar around what will be the gas chamber openings of web 8. As stated, reference numeral 10 refers to rings with a cross-bar being comprised of solder and having a particular contour. They will be interposed between web 8 along the rim that outlines the openings 2, and the rim of the window panes being provided with rings 5, 6, and 7.

One can see in the upper left hand portions of FIG. 1 that there are two window panes 3 with rim portions 4 being provided with these rings of the kind shown in FIG. 2. In between these two panes 3 on one hand and the far side of the webs 8 of frame 1 will be interposed two solder parts 10 which then will join the panes to web 8, not visible in FIG. 1. On the visible side, as far as web 8 is concerned, FIG. 1 shows the web proper, the cross-bar in between, one not yet attached and used solder ring 10 which will be attached to the visible surface of web 8 and to which, in turn, will be connected the one single pane 3 shown in the lower right hand portion of FIG. 1. To the left of this arrangement is shown the already attached fourth pane 3 and one can now see that between the circular pane defining the window and the rim outlining the more or less square-shaped recess for web 8, there are provided four spaces 9 (per window) into which solder will flow.

Soldering will take place in the vapor phase in a chemically inert liquid for various temperatures which differ for one and the other side, whereby the inert liquid matches the solder of the respective parts 10. The front side 11 uses a soldering temperature of about 213° C. and the far side 12 uses a lower temperature of about 170°. The invention is not limited to the embodiments described above but all changes and modifications thereof, not constituting departures from the spirit and scope of the invention, are intended to be included.

We claim:

1. In a Method for making a gas chamber for photometric measuring equipment comprising
    providing a metal frame with recesses on opposite sides establishing a web and at least one opening in the web and having solder surface areas;
    providing at least two calcium fluoride panes, said panes each having a rim portion;
    providing rim surface portions of the panes about to face the recessweb portion of said metal frame with a plurality of layers, by (i) physical vapor depositing a thin chromium nickel layer, (ii) physical vapor depositing thereon a nickel layer, and (iii) by physical vapor depositing thereon a gold layer;
    vapor depositing on said web portion around the opening of said recesses a gold layer;
    providing at least two solder elements of basically ring-shaped configuration respectively to be interposed between the web and the panes for subsequent soldering of the panes to the web portion, and here particularly the gold layer on the web portion to the gold layer as deposited on the respective pane, said solder elements being configured so that between their respective outer contour and walls of the recesses a solder flow space obtains when the solder elements are placed into the recesses; and soldering the ring on one side for solder-connecting the respective pane to the web at a temperature of about 213° C. in an inert gas and soldering the other ring on the other side of and to the web and the respective other pane at a soldering temperature in an inert gas at about 170° C.

2. Method as in claim 1, the steps (i), (ii), (iii) respectively establish layer thicknesses of 50, 200, 30 nanometers, the gold layers on the web being each about 30 nanometers thick.

* * * * *